(12) United States Patent
Iwata

(10) Patent No.: US 12,330,156 B2
(45) Date of Patent: Jun. 17, 2025

(54) FLOW PATH DEVICE, AND TESTING DEVICE AND TESTING METHOD USING SAME

(71) Applicant: Shimadzu Corporation, Kyoto (JP)

(72) Inventor: Hiroshi Iwata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 814 days.

(21) Appl. No.: 17/432,759

(22) PCT Filed: Jan. 9, 2020

(86) PCT No.: PCT/JP2020/000493
§ 371 (c)(1),
(2) Date: Aug. 20, 2021

(87) PCT Pub. No.: WO2020/202688
PCT Pub. Date: Oct. 8, 2020

(65) Prior Publication Data
US 2022/0143614 A1    May 12, 2022

(30) Foreign Application Priority Data
Apr. 2, 2019    (JP) ................... 2019-070836

(51) Int. Cl.
*B01L 3/00* (2006.01)
*C12Q 1/18* (2006.01)
(Continued)

(52) U.S. Cl.
CPC ... *B01L 3/502761* (2013.01); *B01L 3/502715* (2013.01); *B01L 3/502746* (2013.01);
(Continued)

(58) Field of Classification Search
CPC .......... G01N 15/1056; G01N 15/1404; G01N 15/1484; G01N 2015/1006; G01N 21/03;
(Continued)

(56) References Cited

U.S. PATENT DOCUMENTS 9,500,664 B2 * 11/2016 Ness ................... B01F 33/3011
2008/0305537 A1 * 12/2008 Sato .................. B01L 3/502761
427/9

(Continued)

FOREIGN PATENT DOCUMENTS

JP    2018-096703    6/2018

OTHER PUBLICATIONS

International Search Report issued Mar. 24, 2020 in International (PCT) Application No. PCT/JP2020/000493 with English translation.

(Continued)

*Primary Examiner* — Kara E. Geisel
*Assistant Examiner* — Jonathon Cook
(74) *Attorney, Agent, or Firm* — Wenderoth, Lind & Ponack, L.L.P.

(57) ABSTRACT

Provided are a flow path device capable of rapidly performing a drug sensitivity test, and a testing device and a testing method using the same. A flow path device adjusted for observing a test solution existing in a well plate having a well includes: a plate-shaped main body having a main
(Continued)

surface; and an insertion body provided in the main body, the insertion body extending along a direction perpendicular to the main surface of the main body, the insertion body configured to be inserted into the well. The insertion body includes a pore having a dimension capable of sucking up the test solution in the well, and the main body includes an observation flow path which communicates with the pore and extends along a direction in plane with the main surface of the main body.

6 Claims, 6 Drawing Sheets

(51) Int. Cl.
G01N 21/03 (2006.01)
G01N 21/05 (2006.01)
G01N 21/11 (2006.01)
G01N 21/13 (2006.01)
G02B 21/06 (2006.01)
G02B 21/26 (2006.01)

(52) U.S. Cl.
CPC .............. *C12Q 1/18* (2013.01); *G01N 21/03* (2013.01); *G01N 21/05* (2013.01); *G01N 21/11* (2013.01); *G01N 21/13* (2013.01); *G02B 21/06* (2013.01); *G02B 21/26* (2013.01); *B01L 2200/0647* (2013.01); *B01L 2300/0829* (2013.01)

(58) Field of Classification Search
CPC .... G01N 21/05; G01N 21/0303; G01N 21/11; G01N 21/13; G01N 2021/0346; B01L 3/502715; B01L 3/502761; B01L 3/502746; B01L 2200/0647; B01L 2200/027; B01L 2300/0829; B01L 2400/0406; C12Q 1/18; G02B 21/06; G02B 21/26

See application file for complete search history.

(56) References Cited

U.S. PATENT DOCUMENTS

| | | | |
|---|---|---|---|
| 2012/0058571 A1* | 3/2012 | Knight | B01L 3/022 422/524 |
| 2017/0203537 A1* | 7/2017 | Taniguchi | B32B 27/20 |
| 2018/0164569 A1* | 6/2018 | Brinkman | G02B 21/16 |
| 2019/0234961 A1* | 8/2019 | Gentalen | H01J 49/0404 |

OTHER PUBLICATIONS

Written Opinion of International Searching Authority issued Mar. 24, 2020 in International (PCT) Application No. PCT/JP2020/000493 with English translation.

* cited by examiner

FLOW PATH DEVICE, AND TESTING DEVICE AND TESTING METHOD USING SAME

TECHNICAL FIELD

The present invention relates to a flow path device, and a testing device and a testing method using the same.

BACKGROUND ART

In general, a drug sensitivity test which is an efficacy test of an antibacterial drug is performed by a trace liquid dilution method using a well plate (see, for example, Patent Literature 1). In an exemplary trace liquid dilution method, a series of two-fold drug concentration dilutions are prepared for different antibacterial drugs, and after a bacterial culture time of about 18 hours, the concentration of the drug to which the bacteria grow and become cloudy is evaluated to test the growth inhibitory concentration (effective drug concentration) of the antibacterial drug.

On the other hand, in recent years, a method has been proposed in which a drug sensitivity test is performed within a few hours by observing the division and morphological changes of each bacterium instead of the macroscopic growth of the bacteria. In this method, since a microscope is used for observing bacteria of about 1 μm, an integrated micro flow path having parallelism in the vertical direction of the observation area, liquid height, and simultaneous observation performance at multiple points may be used.

CITATION LIST

Patent Literature

Patent Literature 1: JP 2018-096703 A

SUMMARY OF INVENTION

Technical Problem

However, in a case where the integrated micro flow path is used as in the conventional case, the technique of immobilizing the drug in the integrated micro flow path is an issue, and there are problems in maintaining the stability of the rate at which the dry drug elutes and diffuses and drug titer after the injection of a bacterial solution.

In a morphological observation method, it is desirable that the observation is completed before the morphological change of bacteria as a test result occurs. For example, in a case where the morphological change of bacteria as the test result occurs in about one to three hours, the observation time span is desirably about 30 minutes.

However, in a case where the morphology of bacteria is observed using a commercially available well plate, the focal length of the microscope changes according to the volume (liquid height) of the bacterial solution injected into the well plate, so it may be necessary to change the focal position of each well individually. At this time, for example, when the observation is performed with a phase-contrast microscope, it is necessary to focus two components of the objective lens and the phase-contrast capacitor from both the upper and lower directions, which takes time.

For example, in the case of a 96-well plate (24 drugs×4 concentrations), there are many observation points, and it may be difficult to observe in about 30 minutes.

In this regard, an object of the present invention is to provide a flow path device capable of rapidly performing a drug sensitivity test, and a testing device and a testing method using the same.

Solution to Problem

The specification of this application contains the whole content of Japanese Patent Application No. 2019-70836 filed on Apr. 2, 2019.

A first aspect of the present invention relates to a flow path device adjusted for observing a test solution existing in a well plate having a well. The device includes: a plate-shaped main body having a main surface; and an insertion body provided in the main body, the insertion body extending along a direction perpendicular to the main surface of the main body, the insertion body configured to be inserted into the well. The insertion body includes a pore having a dimension capable of sucking up the test solution in the well, and the main body includes an observation flow path which communicates with the pore and extends along a direction in plane with the main surface of the main body.

A second aspect of the present invention relates to a testing device which includes: a table which has optical transparency; a light source which is arranged below the table; and a microscope which is arranged above a test container positioned on the table. The test container includes a well plate and the flow path device arranged on the well plate and the table is movable in at least one of an X-axis direction and a Y-axis direction.

A third aspect of the present invention relates to a testing method. A flow path device adjusted for observing a test solution existing in a well plate having a well includes a plate-shaped main body having a main surface, and an insertion body provided in the main body, the insertion body configured to be inserted into the well, the insertion body includes a pore having a dimension capable of sucking up the test solution in the well, and the main body includes an observation flow path extending along a direction in plane with the main surface. The method includes: preparing the flow path device in which the observation flow path communicates with the pore and making the test solution in the well; superposing the flow path device on the well plate and immersing the insertion body in the test solution; moving the test solution to at least the observation flow path; and observing the observation flow path with a microscope.

Advantageous Effects of Invention

According to the first aspect of the present invention, it is possible to provide a flow path device capable of rapidly performing a drug sensitivity test.

According to the second aspect and the third aspect of the present invention, even in a case where a commercially available well plate is used, the drug sensitivity test can be rapidly performed by using the flow path device of the first aspect.

DESCRIPTION OF EMBODIMENTS

Configuration of Drug Sensitivity Testing Device

Hereinafter, embodiments of the present invention will be described with reference to the drawings.

Figure 1:
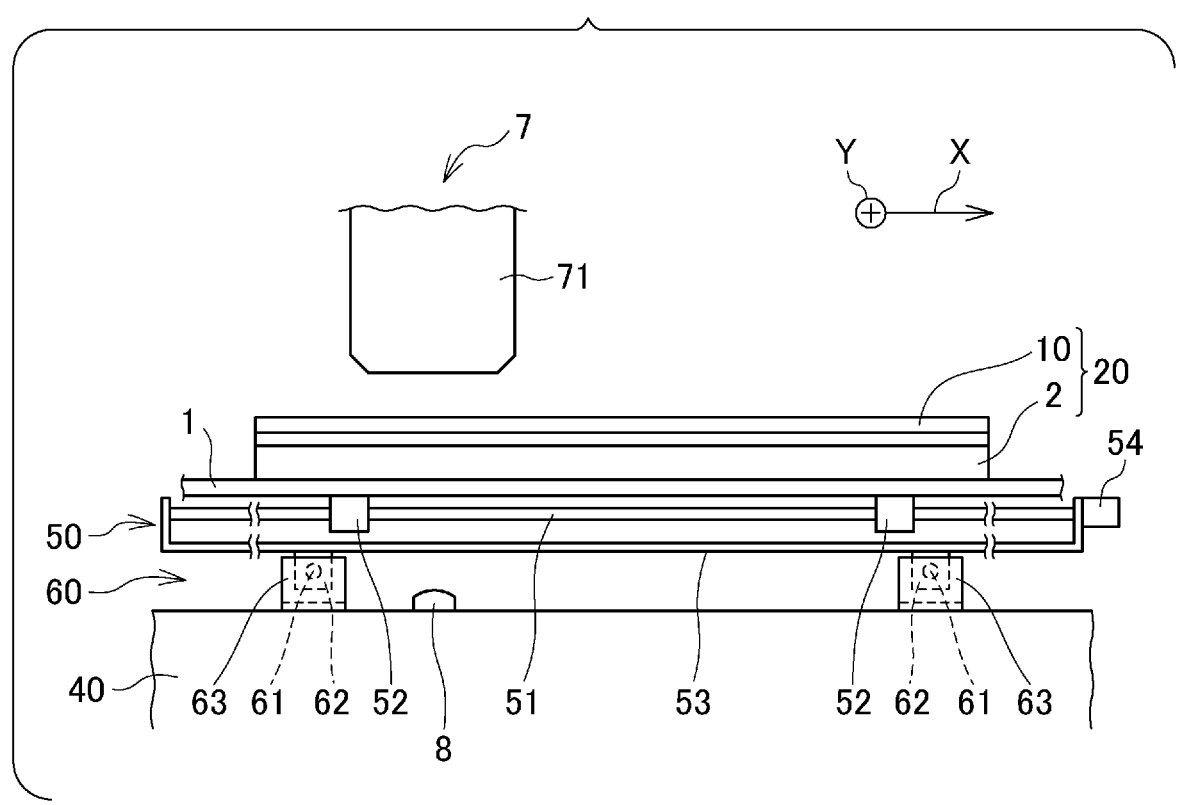
FIG. 1 is a side view illustrating an outline of a drug sensitivity testing device according to an embodiment of the present invention.
Figure 2:
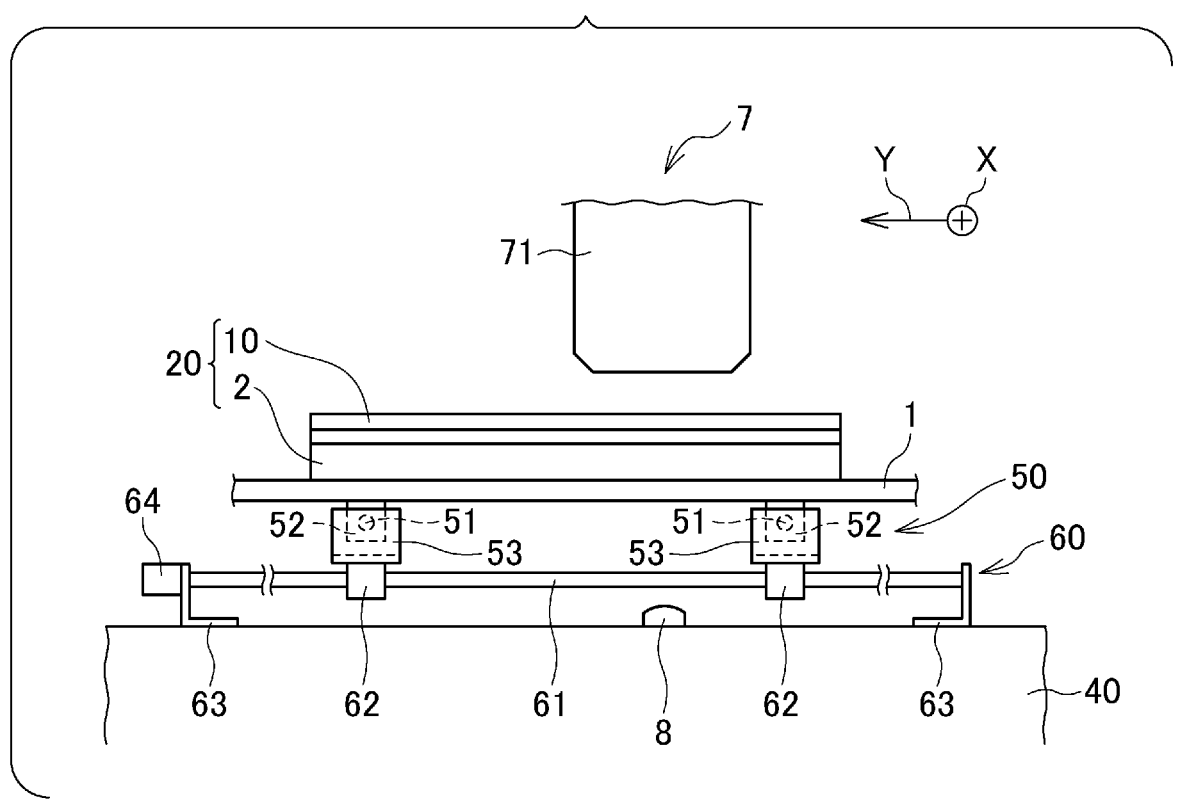
FIG. 2 is a front view of the outline of the drug sensitivity testing device.

FIG. 1 is a side view illustrating an outline of a drug sensitivity testing device, and FIG. 2 is a front view of the outline of the drug sensitivity testing device.

Reference sign 1 indicates a table of the drug sensitivity testing device.

The table 1 is formed of a material having optical transparency. On the table 1, a test container 20 in which a flow path device 10 of this embodiment is superposed on a commercially available well plate 2 is placed in a positioned state. An objective lens 71 of an optical microscope 7 is arranged above the test container 20. A light source 8 is arranged on the upper surface of a base 40 of the drug sensitivity testing device below the objective lens 71. The table 1 is movable in an X-axis direction and a Y-axis direction of FIGS. 1 and 2 in a rectangular coordinate system on a plane.

The drive mechanism of the table 1 is provided under the table 1. The drive mechanism includes an X-axis direction moving unit 50 fixed to the lower surface of the table 1 and a Y-axis direction moving unit 60 fixed to the upper surface of the upper surface of the base 40, and the X-axis direction moving unit 50 is fixed on the Y-axis direction moving unit 60. As illustrated in FIG. 2, the Y-axis direction moving unit 60 includes a pair of first ball screws 61 which extend in the Y-axis direction, first nuts 62 which slide according to the rotation of the first ball screws 61, first supports 63 which support the first ball screws 61, and first stepping motors 64 which are fixed to the first supports 63 and rotate the first ball screws 61. Further, the first support 63 is fixed to the upper surface of the base 40. As illustrated in FIG. 1, the X-axis direction moving unit 50 includes a pair of second ball screws 51 which extend in the X-axis direction, second nuts 52 which slide according to the rotation of the second ball screws 51, second supports 53 which support the second ball screws 51, and second stepping motors 54 which are fixed to the second supports 53 and rotate the second ball screws 51. Further, the second support 53 is fixed on the first nut 62.

Configuration of Test Container

Figure 3:
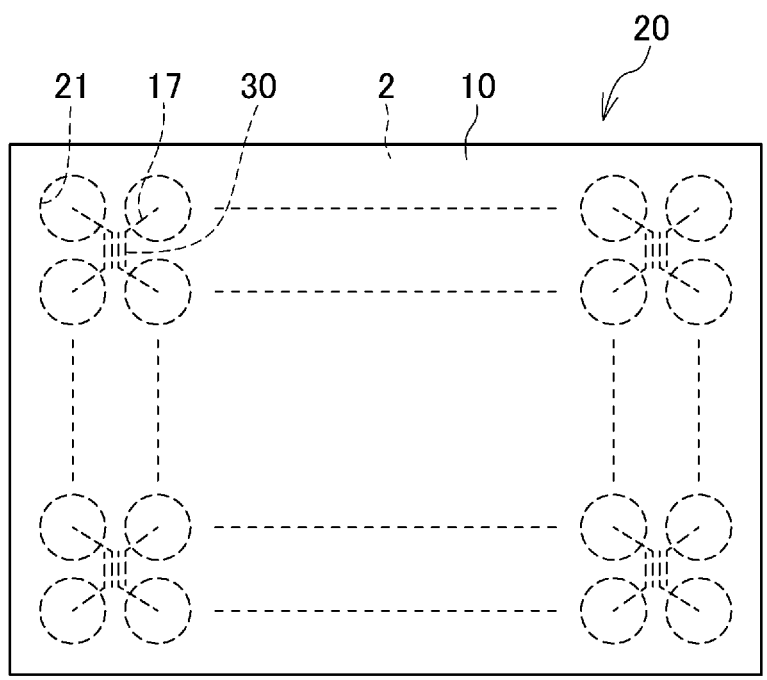
FIG. 3 is a plan view of a test container.
Figure 4:
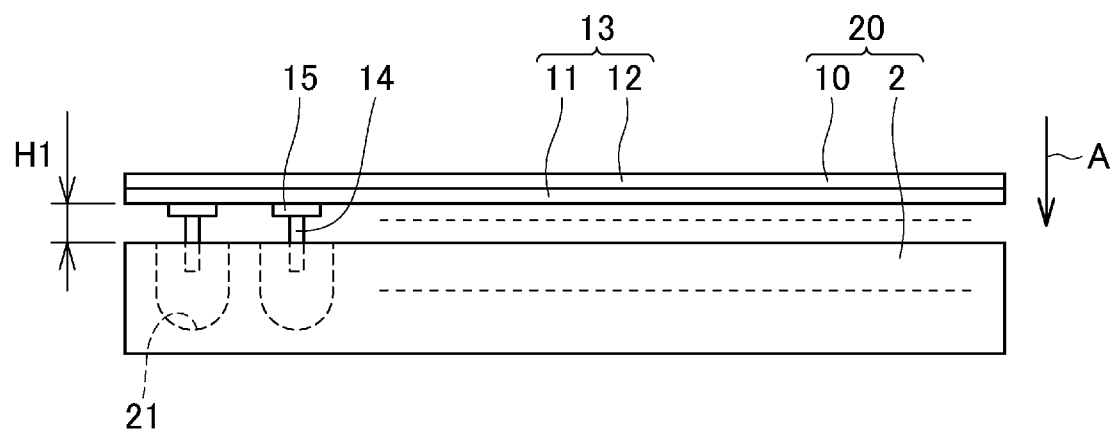
FIG. 4 is a side view of the test container.

FIG. 3 is a plan view of the test container 20, and FIG. 4 is a side view of the test container. In FIG. 3, a micro flow path 17 and a well 21 are partially omitted. In FIG. 4, an insertion body 14, a flange 15, and the well 21 are partially omitted.

The test container 20 is configured by superposing the flow path device 10 of this embodiment on the well plate 2 which is generally commercially available. For example, in the case of a 96-well plate (24 drugs×4 concentrations), the well plate 2 has 96 (8×12) wells 21 in the vertical and horizontal directions, and in all the wells 21, bacteria and antibacterial drugs are mixed. The mixed solution becomes, after several hours, a test solution to be tested.

Configuration of Flow Path Device

Next, the flow path device 10 will be described.

Figure 5:
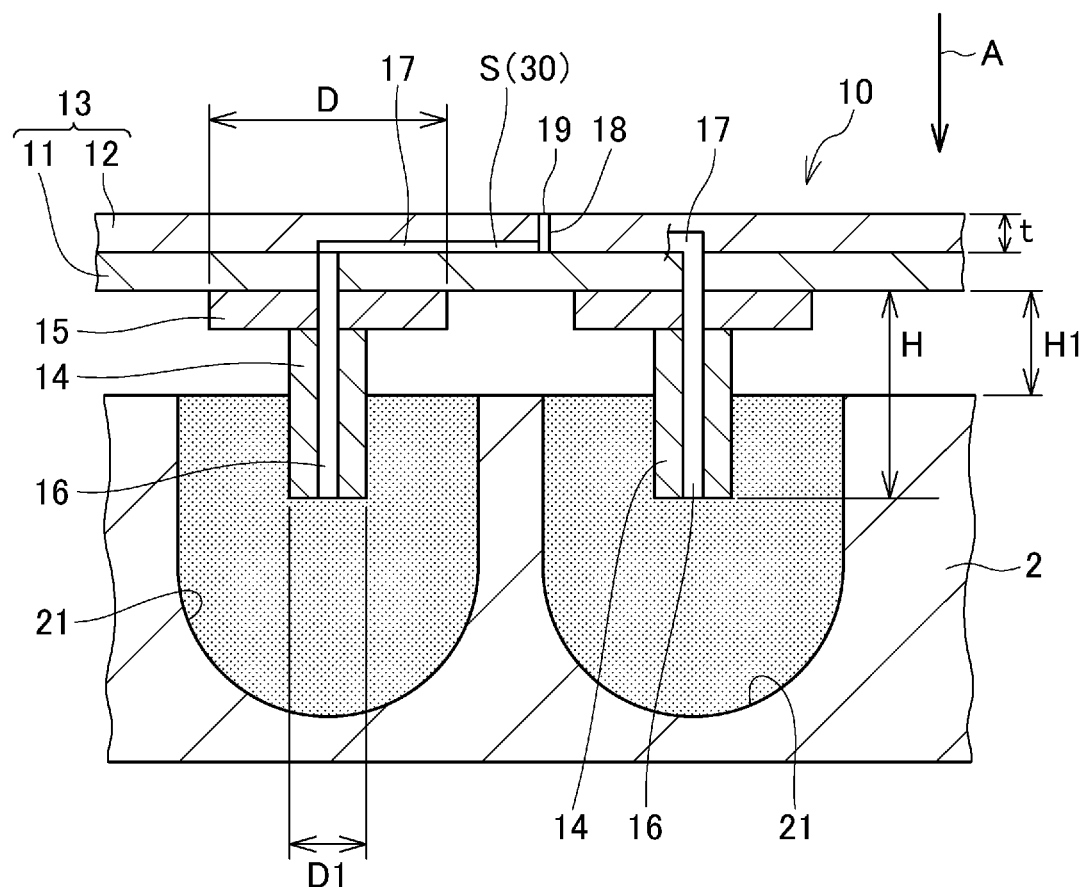
FIG. 5 is a cross-sectional view illustrating an outline for explaining a flow path device.
Figure 6:
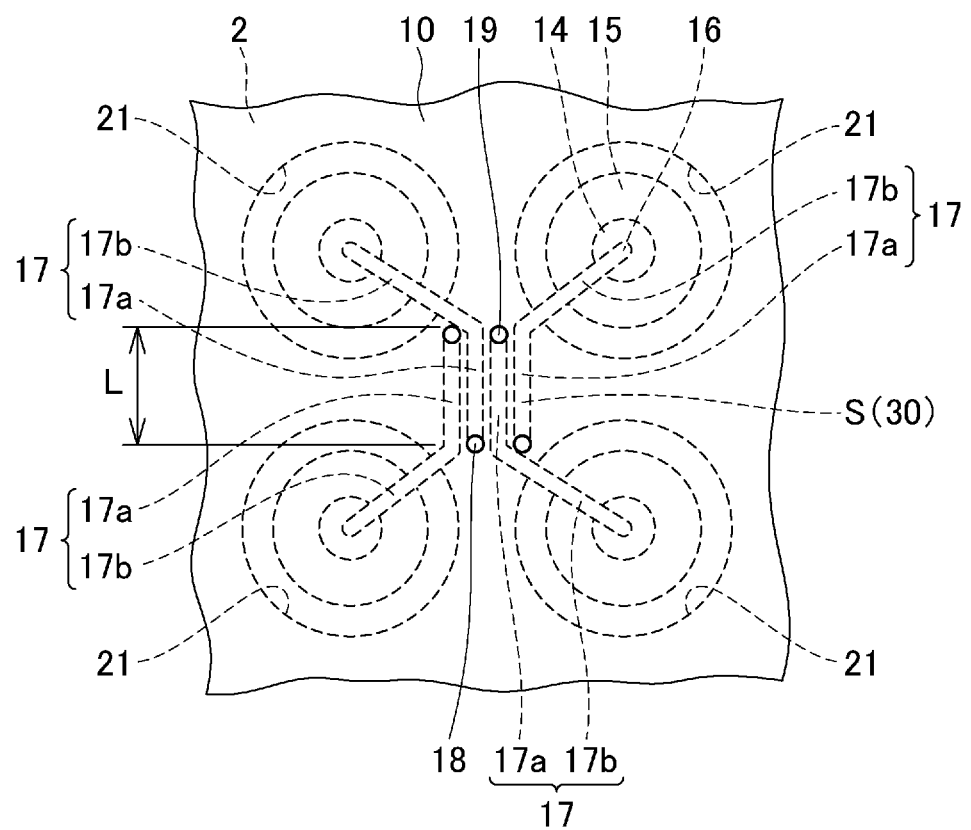
FIG. 6 is a plan view illustrating the outline for explaining the flow path device.

FIG. 5 is a cross-sectional view illustrating an outline for explaining the flow path device 10, and FIG. 6 is a plan view of the outline for explaining the flow path device 10. In FIG. 5, a cross section is taken along one flow path communicating from the well 21 on the left side, and the flow path communicating from the well 21 on the right side is illustrated only halfway through the micro flow path 17. In this embodiment, when the test is performed, changes in the test solutions in the four wells 21 can be simultaneously observed with the microscope 7 (see FIG. 1).

The flow path device 10 includes a main body 13 in which a first plate 11 and a second plate 12 having optical transparency and having a thickness t of about 1 mm are superposed vertically and the insertion body 14 which is provided in the main body 13 and has a diameter D1 of about 2 mm. A length H from the lower surface of the first plate 11 to the tip surface of the insertion body 14 is about 9 mm, and when the flow path device 10 is superposed on the well plate 2, the tip of the insertion body 14 is immersed in the test solution in the well 21 and does not reach the bottoms of the well 21. Incidentally, in this embodiment, the main body 13 has upper and lower surfaces orthogonal to the direction of arrow A as main surfaces.

Reference sign 15 is a flange having a diameter D of about 5 mm which is slightly smaller than the opening inner diameter (7 mm) of the well 21. When the flow path device 10 is superposed on the well plate 2, the flange 15 is inserted into the well 21 to prevent a large relative deviation between the flow path device 10 and the well plate 2.

Although not illustrated, the insertion body 14 and the flange 15 are provided according to the number and arrangement of the wells 21. The well plate 2 is a commercially available 96-well plate (24 drugs×4 concentrations), and the first plate 11 of the main body 13 is provided with 96 insertion bodies 14 and 96 flanges 15.

All insertion bodies 14 have pores 16 for sucking up the test solution in the wells 21 by capillarity. The pore 16 penetrate the flange 15 and the first plate 11. The micro flow path 17 communicates with the pore 16. The micro flow path 17 is formed on the joint surface (the interface between the first plate 11 and the second plate 12) of the first plate 11 with the second plate 12. The micro flow path 17 communicates with an opening 19 communicating with the outside of the flow path device 10 through an exhaust hole 18 extending vertically. As illustrated in FIG. 6, the micro flow path 17 is provided to extend along the main surface direction of the main body 13, and is configured by an observation flow path 17a and an introduction flow path 17b. The pore 16 and the observation flow path 17a are connected by the introduction flow path 17b. Further, the exhaust hole 18 is connected to the observation flow path 17a.

In this embodiment, when the flow path device 10 is lowered by a dimension H1 in the direction of arrow A in FIG. 5, and the flow path device 10 is superposed on the well plate 2, the insertion body 14 and the flange 15 are inserted into the well 21, and the insertion body 14 is immersed in the test solution of the well 21. Further, the test solution sucked up by the capillarity is sucked up to reach the exhaust hole 18 through the pores 16 of the insertion body 14, and the test solution is filled in the micro flow path 17.

Therefore, in a case where the morphological observation of bacteria is performed using a commercially available well plate 2, even when the volume (liquid height) of the test solution in the 96 wells 21 of the well plate 2 varies, the focal length of the microscope 7 does not change since the test solution in the micro flow path 17 is observed. It is not necessary to change the focal position of each well 21 individually. For example, when observation is performed with a phase-contrast microscope, it is not necessary to focus an objective lens and a phase-contrast capacitor from both the upper and lower directions, and it does not take time to focus.

FIG. 6 illustrates a state where changes in the test solution in the four wells 21 can be simultaneously observed by the microscope 7. In this embodiment, 96 insertion bodies 14 are provided corresponding to the number of wells 21. However, only four insertion bodies 14 are described in FIG. 6. The other insertion bodies 14 have the same configuration, and the description thereof is omitted.

The insertion bodies 14 have the pores 16, respectively, and observation flow paths 17a of the four micro flow paths 17 communicating with the pores 16 are arranged together close to each other in parallel in a substantially horizontal plane S. The substantially horizontal plane S in which the observation flow paths 17a are put together is regarded as an observation part 30 of the test solution.

The observation part 30 has a narrow range such that changes in the test solution guided to the four micro flow paths 17 can be simultaneously observed by the microscope 7.

In the flow path device 10, a flow path length from the tip of each insertion body 14 to the observation part 30 is set to be equal in all the insertion bodies 14.

In this embodiment, changes in the test solution guided to the four micro flow paths 17 can be simultaneously observed by the microscope 7. Therefore, a plurality of (four in this embodiment) observation points can be included within one field of view of the microscope 7, and the number of times of imaging can be reduced. Further, when the plurality of observation points are included within one field of view of the microscope 7, it is possible to easily compare the plurality of observation points.

The inner diameters of the pores 16 and the micro flow paths 17 are usually set within a range of 1 μm to 1 mm. This inner diameter is determined by the viscosity of the test solution and the like. Among them, the inner diameter of the observation flow path 17a is preferably 50 μm or less from the viewpoint of easy observation of bacterial morphology. The observation flow path 17a is preferably linear from the viewpoint of easy observation of bacterial morphology. The length L of the observation part 30 is about 3 mm.

Compared with the case of using the integrated micro flow path as in the conventional case, the concentration change due to drug diffusion can be ignored. A rapid test can be performed using the commercially available well plate 2 for testing sensitivity, which is advantageous in terms of cost and does not impair reliability of a drug concentration or the like.

Testing Method

Next, a testing method will be described.

First, in the well 21 of the well plate 2, the bacteria and the antibacterial drugs are mixed, and then, after several hours, the mixed solution is used as the test solution to be tested.

Next, the flow path device 10 is superposed on the well plate 2, and the insertion body 14 of the flow path device 10 is immersed in the test solution.

Next, utilizing the capillarity, the test solution is sucked up through the pore 16 of the insertion body 14 to reach the exhaust hole 18, and the micro flow path 17 is filled with the test solution.

Then, the test container 20 in which the flow path device 10 is superposed on the well plate 2 is placed on the table 1 of the drug sensitivity testing device.

Next, the table 1 is moved by the drive mechanism of the table 1 so that the first observation part 30 is positioned below the microscope 7, and the first observation part 30 is imaged by the microscope 7 to observe the morphology of the bacteria in the micro flow path 17 of the first observation part 30.

Thereafter, the table 1 is moved again, and the morphology of the bacteria in the micro flow path 17 of the second observation part 30 is observed in the same manner. This is repeated in sequence, and the morphology of the bacteria is observed in a plurality of observation parts 30.

Effect

As described above, the flow path device 10 of this embodiment can be used in the state of being superposed on the commercially available well plate 2, and thus the cost of morphological observation can be reduced.

Further, the flow path device 10 of this embodiment is superposed on the well plate 2 so that the test solution in the well 21 is moved to the observation part 30 in the micro flow path 17 of the flow path device 10, and the morphology of the bacteria in 30 can be observed with the microscope 7. Therefore, unlike morphological observation of the test solution in the well 21 by the microscope 7, there are no factors, such as variations in the volume (the height of a test solution level) of the test solution and the curvature of the test solution level, which require time for focusing, and the time required for the morphological observation of bacteria can be shortened.

Further, in the flow path device 10 of this embodiment, the observation part 30 is on the substantially horizontal plane S, and thus it is easy to observe with the microscope 7.

Further, since the micro flow path 17 is formed on the joint surface of the first plate 11 with the second plate 12, all the observation parts 30 are at the same height position. Therefore, the focusing time of the microscope 7 can be shortened.

In particular, in the flow path device 10 of this embodiment, an area in which the four micro flow paths 17 are arranged together close to each other in parallel is used as the observation part 30, and thus the four observation points can be included within one field of view of the microscope 7, and the number of times of imaging can be reduced.

In the flow path device 10 of this embodiment, bacteria and drugs such as antibacterial drugs are not mixed in the micro flow path 17, and thus the concentration of the test solution does not change due to drug diffusion so that the test reliability is excellent.

Other Embodiments

In the above-described embodiment, four micro flow paths 17 are arranged together to form the observation part 30, but the number of the micro flow paths 17 to be combined may be two, three, or five or more.

However, as in the above-described embodiment, it is preferable that the micro flow paths 17 to be combined are from four wells 21, and the observation part 30 is arranged at the center of the four wells. The reason is that the flow path length from the tip of the insertion body 14 to the observation part 30 can be easily made equal in all the flow paths, and the time for the test solution to move to the observation part 30 can be made equal.

On the other hand, the observation points may be arranged separately from each other without the plurality of observation points being brought close to each other.

Moreover, in the above-described embodiment, the test solution is moved to the observation part 30 by utilizing the capillarity, but other units may be used. For example, when partition is made into a first space where the opening 19 of the exhaust hole 18 is positioned and a second space where the liquid level of the test solution of the well plate 2 is positioned, the air pressure in the first space is lowered, and a negative pressure is applied to the opening 19 of the exhaust hole 18, the test solution may be sucked up and be moved to the observation part 30. Alternatively, the test solution may be pushed out and moved to the observation part 30 by increasing the air pressure in the second space and pressurizing the liquid level of the test solution. Alternatively, both of them (lowering the air pressure in the first space and increasing the air pressure in the second space) may be used.

Incidentally, the above-described embodiment is merely an example of the aspect of the present invention, and can be arbitrarily modified and applied without departing from the gist of the present invention.

ASPECTS

It is understood by those skilled in the art that the above-described embodiment is a specific example of the following aspects.

(First item) A flow path device 10 according to a first aspect is the flow path device 10 adjusted for observing a test solution existing in a well plate 2 having a well 21. The device may include: a plate-shaped main body 13 having a main surface; and an insertion body 14 provided in the main body 13, the insertion body extending along a direction perpendicular to the main surface of the main body 13, the insertion body configured to be inserted into the well 21. The insertion body 14 may include a pore 16 having a dimension capable of sucking up the test solution in the well 21, and the main body 13 may include an observation flow path 17a which communicates with the pore 16 and extends along a direction in plane with the main surface of the main body 13.

According to the flow path device 10 described in the first item, it is possible to provide a flow path device capable of rapidly performing a drug sensitivity test.

(Second item) In the flow path device 10 according to the first item, the main body 13 may include a first plate 11 and a second plate 12, and the micro flow path 17 may be formed at an interface between the first plate 11 and the second plate 12.

According to the flow path device described in the second item, the micro flow path 17 can be easily formed.

(Third item) In the flow path device 10 according to the second item, a plurality of the observation flow paths 17a may be arranged close to each other in a predetermined area to form an observation part 30, and flow path lengths from respective tips of a plurality of the insertion bodies 14 to the observation part 30 may be set to be equal.

According to the flow path device 10 described in the third item, the time for the test solution to move to the observation part 30 can be set to be equal.

(Fourth item) In the flow path device 10 according to the third item, the plurality of observation flow paths 17a of the observation part 30 may be arranged in parallel.

According to the flow path device 10 described in the fourth item, a plurality of observation points can be easily included within one field of view of the microscope 7. Therefore, it becomes easier to compare the plurality of observation points.

(Fifth item) In the flow path device 10 according to any one of the first to fourth items, a direction in which the pore 16 extends may be orthogonal to the observation flow path 17a.

According to the flow path device 10 described in the fifth item, the test solution can be easily held in the observation flow path 17a.

(Sixth item) A testing device according to a second aspect may include: a table 1 which has optical transparency; a light source 8 which is arranged below the table 1; and a microscope 7 which is arranged above a test container 20 positioned on the table 1. The test container 20 may include a well plate 2 and the flow path device 10 arranged on the well plate 2 and described in any one of the first to fifth items 1 to 5, and the table 1 may be movable in at least one of an X-axis direction and a Y-axis direction.

According to the testing device described in the sixth item, by using the flow path device 10 according to any one of the first to fifth items, morphological observation can be performed quickly and stably even in a case where the commercially available well plate 2 is used.

(Seventh item) In a testing method according to a third aspect, a flow path device 10 adjusted for observing a test solution existing in a well plate 2 having a well 21 may include a plate-shaped main body 13 having a main surface, and an insertion body 14 provided in the main body 13, the insertion body configured to be inserted into the well 21, the insertion body 14 may include a pore 16 having a dimension capable of sucking up the test solution in the well 21, and the main body 13 may include an observation flow path 17a extending along a direction in plane with the main surface. The method may include: preparing the flow path device 10 in which the observation flow path 17a communicates with the pore 16 and making the test solution in the well 21; superposing the flow path device 10 on the well plate 2 and immersing the insertion body 14 in the test solution; moving the test solution to at least the observation flow path 17a; and observing the observation flow path 17a with a microscope 7.

According to the testing method described in the seventh item, by using the flow path device 10, morphological observation can be performed quickly and stably even in a case where the commercially available well plate 2 is used.

REFERENCE SIGNS LIST

1 Table
2 Well plate
7 Objective lens
8 Light source
10 Flow path device
11 First plate
12 Second plate
13 Main body
14 Insertion body
16 Pore
17 Micro flow path
18 Exhaust hole
19 Opening
20 Test container
21 Well
30 Observation part

The invention claimed is:

1. A flow path device adjusted for observing a test solution existing in a well in a well plate, the flow path device comprising:
a plate-shaped main body having an upper surface and a lower surface as main surfaces; and
an insertion body provided in the main body, the insertion body extending along a direction perpendicular to the main surfaces of the main body, the insertion body having a pore, the insertion body being configured to be inserted into the well, wherein the pore has a dimension capable of sucking up the test solution in the well by capillarity, the pore extends from a tip of the insertion body to a first position between the upper surface and the lower surface of the main body, and the main body includes:

an observation flow path which extends from a first end to a second end within a plane parallel to the main surfaces, the observation flow path having a predetermined flow path length, wherein the first end of the observation flow path communicates with a portion of the pore at the first position; and an exhaust hole extending from the second end of the observation flow path to the upper surface of the main body in a direction orthogonal to the observation flow path, wherein the exhaust hole is connected to an opening communicating with an outside of the flow path device.

2. The flow path device according to claim 1, wherein the main body includes a first plate and a second plate, and the observation flow path is formed at an interface between the first plate and the second plate.

3. The flow path device according to claim 2, wherein the observation flow path is one of a plurality of the observation flow paths, the plurality of the observation flow paths being arranged adjacent to each other in a predetermined area to form an observation part, and the insertion body is one of a plurality of the insertion bodies, and flow path lengths from respective tips of the plurality of the insertion bodies to the observation part are set to be equal.

4. The flow path device according to claim 3, wherein the plurality of observation flow paths of the observation part are arranged in parallel.

5. A testing device comprising:

a table which has optical transparency;

a light source which is arranged below the table; and a microscope which is arranged above a test container positioned on the table, wherein the test container includes a well plate and the flow path device arranged on the well plate and according to claim 1, and the table is movable in at least one of an X-axis direction and a Y-axis direction.

6. A testing method, wherein a flow path device adjusted for observing a test solution existing in a well in a well plate includes a plate-shaped main body having an upper surface and a lower surface as main surfaces, and an insertion body provided in the main body, the insertion body extending along a direction perpendicular to the main surfaces of the main body, the insertion body being configured to be inserted into the well, the insertion body includes a pore having a dimension capable of sucking up the test solution in the well by capillarity, the pore extending from a tip of the insertion body to a first position between the upper surface and the lower surface of the main body, and the main body includes:

an observation flow path which extends from a first end to a second end within a plane parallel to the main surfaces, the observation flow path having a predetermined flow path length, wherein the first end of the observation flow path communicates with a portion of the pore at the first position; and an exhaust hole extending from the second end of the observation flow path to the upper surface of the main body in a direction orthogonal to the observation flow path, wherein the exhaust hole is connected to an opening communicating with an outside of the flow path device, the method comprising:

preparing the flow path device in which the observation flow path communicates with the pore and making the test solution in the well;

superposing the flow path device on the well plate and immersing the insertion body in the test solution;

moving the test solution to at least the observation flow path; and observing the observation flow path with a microscope.

* * * * *